US012766322B2

(12) United States Patent
Zhou et al.

(10) Patent No.: US 12,766,322 B2
(45) Date of Patent: Oct. 20, 2026

(54) STIMULATOR CIRCUIT, A SYSTEM FOR PROVIDING A STIMULATION OF A BRAIN AND/OR A NERVE, AND A METHOD FOR PROVIDING A COMPENSATED STIMULATION SIGNAL

(71) Applicant: Stichting IMEC Nederland, Eindhoven (NL)

(72) Inventors: Meiyi Zhou, Eindhoven (NL); Haoming Xin, Eindhoven (NL); Roland Van Wegberg, Oss (NL)

(73) Assignee: STICHTING IMEC NEDERLAND, Eindhoven (NL)

( * ) Notice: Subject to any disclaimer, the term of this patent is extended or adjusted under 35 U.S.C. 154(b) by 168 days.

(21) Appl. No.: 18/933,130

(22) Filed: Oct. 31, 2024

(65) Prior Publication Data

US 2025/0144417 A1 May 8, 2025

(30) Foreign Application Priority Data

Nov. 3, 2023 (EP) .................................... 23207587

(51) Int. Cl.
*A61N 1/36* (2006.01)

(52) U.S. Cl.
CPC ....... *A61N 1/36034* (2017.08); *A61N 1/3603* (2017.08); *A61N 1/36142* (2013.01)

(58) Field of Classification Search
None
See application file for complete search history.

(56) References Cited

U.S. PATENT DOCUMENTS

| | | | | |
|---|---|---|---|---|
| 9,566,449 | B2 | 2/2017 | Perryman et al. | |
| 9,700,724 | B2 * | 7/2017 | Liu | A61N 1/3615 |
| 2008/0015641 | A1 * | 1/2008 | Armstrong | A61N 1/36153 607/2 |
| 2012/0283800 | A1 | 11/2012 | Perryman et al. | |
| 2016/0045743 | A1 | 2/2016 | Liu et al. | |

(Continued)

OTHER PUBLICATIONS

Grossman, et al: "Noninvasive Deep Brain Stimulation via Temporally Interfering Electric Fields", Cell 169, pp. 1029-1041, 2017.

(Continued)

*Primary Examiner* — Kennedy Schaetzle
(74) *Attorney, Agent, or Firm* — MOSER TABOADA

(57) ABSTRACT

A stimulator circuit for generating a stimulation signal comprises: a stimulation signal generating unit for generating and providing a stimulation signal to an output of the stimulator circuit, wherein the stimulation signal comprises a sequence of temporally separated bursts, each comprising an alternating current, AC, signal; a compensation unit configured to, during a burst, generate and provide a compensation current signal for charge balancing to the output for compensating an unbalanced charge of the stimulation signal and forming a compensated stimulation signal at the output, wherein the compensation unit determines the compensation current signal based on a common mode voltage of the stimulation signal and a reference voltage; and a control unit configured to control the reference voltage in dependence of a remaining offset voltage at the output between bursts.

15 Claims, 5 Drawing Sheets

(56) References Cited

U.S. PATENT DOCUMENTS

| | | | | |
|---|---|---|---|---|
| 2023/0173273 | A1 | 6/2023 | Weerakoon et al. | |
| 2023/0201616 | A1* | 6/2023 | Carlson .............. | A61N 1/36002<br>607/76 |

OTHER PUBLICATIONS

Sooksood, et al., "An Active Approach for Charge Balancing in Functional Electrical Stimulation", IEEE Transactions on Biomedical Circuits and Systems, vol. 4, No. 3, pp. 162-170, 2010.

Extended European Search Report for Application No. EP23207587.9 dated Mar. 27, 2024, 6 pages.

* cited by examiner

STIMULATOR CIRCUIT, A SYSTEM FOR PROVIDING A STIMULATION OF A BRAIN AND/OR A NERVE, AND A METHOD FOR PROVIDING A COMPENSATED STIMULATION SIGNAL

CROSS-REFERENCE TO RELATED APPLICATION

The present application claims the benefit of and priority to EP Patent Application Serial No. 23207587.9, filed Nov. 3, 2023, the entire contents of which is incorporated herein by reference.

TECHNICAL FIELD

The present description relates to a stimulator circuit. The present description further relates to a stimulator circuit which may be used in a system for providing stimulation of a brain and/or a nerve and, in particular, in a system for providing temporal interference stimulation of the brain and/or the nerve. The present description also relates to a method that may be performed in a stimulator circuit.

BACKGROUND

Electrical stimulation is widely used in clinical practice. Stimulation may typically be delivered using biphasic charge balanced pulses.

When an accurate spatial selectivity of stimulation is desired, interferential stimulation based on two or more stimulation signals may be used. Interference of the two or more stimulation signals may thus generate an interferential stimulation signal within tissue, which allows selectively stimulating a location within the tissue.

However, the stimulation signals for forming the interferential stimulation may be continuously provided for a long period of time. There is a need to ensure charge balancing in order to avoid safety issues in relation to electrodes and/or tissue.

In addition, in order to avoid large accumulation of offset voltage onto an electrode over several bursts, a reset switch may be used for removing the offset voltage between bursts of the stimulation signal (periods when the stimulation signal is output to the electrode). However, a reset process may require a relatively long recovery time before the electrode may be used for output of a new stimulation signal or before recording of a neural signal may be performed.

SUMMARY

An objective of the present description is to ensure charge balancing in stimulation that is to be provided to a subject. A particular objective is to ensure charge balancing while avoiding or reducing recovery time between bursts of the stimulation signal.

These and other objectives are at least partly met by the invention as defined in the independent claims. Preferred embodiments are set out in the dependent claims.

According to a first aspect, there is provided a stimulator circuit for generating a stimulation signal, said stimulator circuit comprising: a stimulation signal generating unit configured to generate a stimulation signal and provide the stimulation signal to an output of the stimulator circuit, wherein the stimulation signal comprises a sequence of temporally separated bursts, wherein each burst comprises an alternating current (AC) signal having a sinusoidal-like waveform; a compensation unit configured to, during a burst of the stimulation signal, generate a compensation current signal for charge balancing and provide the compensation current signal to the output of the stimulator circuit for compensating an unbalanced charge of the stimulation signal and forming a compensated stimulation signal at the output of the stimulator circuit, wherein the compensation unit is configured to determine the compensation current signal based on a common mode voltage of the stimulation signal and a reference voltage; and a control unit configured to control the reference voltage in dependence of a remaining offset voltage at the output of the stimulator circuit between bursts of the stimulation signal.

A mismatch between positive and negative parts of a waveform may cause an unbalanced charge to electrodes connected to the stimulator circuit. The unbalanced charge may introduce an offset voltage build-up onto the electrodes over time, in particular as an interface between electrode and tissue is often very capacitive. If the stimulator circuit is used to continuously output a burst for a long period of time, the unbalanced charge can cause safety issues to the electrode and/or the tissue. For instance, the offset voltage build-up may form such a large electrical field that electrical breakdown of water occurs. The offset voltage build-up may also cause the electrode to break such that a subject to the stimulation may be exposed to toxic substances.

Thanks to the compensation current signal provided by the stimulator circuit, any unbalanced charge may be compensated during each burst of the stimulation signal. Thus, the stimulator circuit may allow the burst to be output continuously for a long period of time without any need to interrupt stimulation in order for charge balance compensation to be performed.

Thanks to the stimulator circuit, a compensation unit is used for compensating an unbalanced charge of the stimulation signal. The stimulator circuit may thus ensure that charge balancing is provided so as to compensate for any mismatch between positive and negative parts of the waveform of the stimulation signal. This implies that the stimulator circuit may provide compensation instead of (or in combination with) control of functionality of components of the stimulator circuit.

The stimulation signal generating unit may comprise components having nonideal function which may cause an unbalance in the waveform. If the stimulation signal generating unit is to be provided in an integrated circuit, compensation of nonideal function of components may be difficult or impossible to achieve in the integrated circuit. Thanks to providing the compensation unit, the stimulator circuit may still ensure that an unbalanced charge is compensated to improve safety of the stimulator circuit. Hence, the stimulator circuit may be provided in an integrated circuit providing a very small form factor of the stimulator circuit.

In addition to offset voltage build-up during bursts, offset voltage build-up may accumulate during a sequence of bursts. Thanks to the control of the reference voltage, any offset voltage build-up over a sequence of bursts may be compensated for. This may be done without a need for using any reset switch and without any associated recovery time before the electrode may be used. Hence, the stimulation circuit is able to provide compensation of offset voltage build-up in a reset-free and recovery-free manner.

This implies that timing of recording of a signal from tissue being stimulated is not affected by any reset. While a reset of an offset voltage on the electrode may conventionally be performed immediately after a burst, no such reset is needed in use of the stimulator circuit. This implies that recording of a signal, e.g., a signal in a brain and/or nerve being stimulated, may be performed immediately after the burst of the stimulation signal. The recording of the signal is not affected by any reset artifact since no reset process need be performed.

Instead of using a reset process, the stimulation circuit is configured to use a controllable reference voltage. The reference voltage is used by the compensation unit in order to provide compensation of offset voltage build-up during bursts. However, by changing the reference voltage in dependence of the remaining offset voltage after a burst, the compensation unit may be controlled such that, during a coming burst, the compensation current signal generated by the compensation unit compensates for the remaining offset voltage. This is achieved since the compensation unit determines the compensation current signal based on the reference voltage, such as based on a difference between the common mode voltage and the reference voltage. When the reference voltage is changed, the compensation unit may regulate the offset voltage and generate the compensation current signal based on the difference between the common mode voltage and the changed reference voltage.

The stimulation signal may be used for stimulating a brain and/or a nerve of a living being. For instance, the stimulation signal may be used for triggering a neural signal to be generated in the brain and/or the nerve or for blocking a neural signal that is propagating in the brain and/or the nerve.

The stimulator circuit may be particularly useful for generating stimulation signals that are to be used for temporal interference stimulation, wherein multiple stimulation signals interfere for causing an interferential signal within a brain and/or a nerve to be stimulated, such that the interferential signal may provide a desired stimulation. The temporal interference stimulation allows spatially selecting a location to be stimulated.

In temporal interference stimulation, stimulation may be provided continuously over relatively long time and/or with a large number of bursts of individual stimulation signals. In order to avoid crosstalk between different stimulation signals, independent current source and current sink may be used for each stimulator circuit. This implies that there is a high risk of mismatch between the current source and the current sink such that build-up of an offset voltage onto electrodes may be likely. Thus, use of the stimulator circuit according to the first aspect may ensure that offset voltage build-up in temporal interference stimulation is avoided.

The AC signal having a sinusoidal-like waveform implies that the AC signal may be sinusoidal but does not necessarily need to be a pure sinusoidal waveform. For instance, the AC signal may be a pseudo-sinusoidal waveform, a modified sinusoidal waveform, or a multi-level waveform approximating a sinusoidal waveform.

The stimulation signal generating unit may output a current signal. The current signal may be converted to a voltage signal by being output to an electrode connected to tissue. Thus, the compensation unit may be configured to monitor a common mode voltage based on a stimulation signal which may be a current signal. The compensation unit may further output a compensation current signal that compensates an unbalanced charge of the stimulation current signal.

The stimulation signal is provided at the output of the stimulator circuit. Based on the stimulation signal, the compensation current signal is generated and also provided at the output of the stimulator circuit. Thus, the compensation current signal is combined with the stimulation signal at the output of the stimulator circuit to define the compensated stimulation signal. Hence, forming of the compensated stimulation signal may involve combining the stimulation signal at the output of the stimulator circuit with the compensation current signal.

The remaining offset voltage is a voltage that remains at the output of the stimulator circuit between bursts. Thus, the remaining offset voltage is the offset voltage immediately after end of a burst and which remains during a period between bursts. The control unit controls the reference voltage such that the compensation unit, during a following burst, will provide compensation to remove the remaining offset voltage.

It should be realized that a relation between the reference voltage (controlled by the control unit) and the remaining offset voltage may be defined in many different manners. Thus, the reference voltage being controlled in dependence of the remaining offset voltage allows for many different functions between the reference voltage and the remaining offset voltage to be used. An inverse linear relationship between the reference voltage and the remaining offset voltage may be used. However, it should be realized that other functions may be used. For instance, the reference voltage may have a fixed default value, which may not be altered as long as the remaining offset voltage is within a range of allowable values (safe window). Thus, as long as the remaining offset voltage is within the safe window, no action may be needed by the control unit. When the remaining offset voltage is outside the safe window, the reference voltage may be adjusted from the fixed default value by a predefined compensation value.

According to an embodiment, the control unit comprises an offset voltage detection element, wherein the offset voltage detection element is connected to the output of the stimulator circuit for detecting the remaining offset voltage.

Thus, the remaining offset voltage may be detected for allowing control of the reference voltage in dependence of the remaining offset voltage.

The offset voltage detection element may comprise a resistor voltage divider for detecting the remaining offset voltage. Thus, the offset voltage detection element may be a passive component which may require low power consumption.

According to an alternative, the offset voltage detection element may comprise an active voltage detector for detecting the remaining offset voltage. This may allow more accurate detection of the remaining offset voltage compared to using a passive component.

According to an embodiment, the control unit further comprises an adaptation unit, which is configured to output the reference voltage to the compensation unit based on the detected remaining offset voltage.

The adaptation unit may thus provide the reference voltage to be used by the compensation unit, so as to provide control of the reference voltage.

According to an embodiment, the control unit further comprises a logic control programmed to determine reference voltage compensation based on the detected remaining offset voltage, wherein the logic control is configured to control the adaptation unit based on the determined reference voltage compensation.

The use of a logic control may provide an efficient manner of implementing control of the reference voltage in dependence of the remaining offset voltage. The logic control may be programmed to provide a desired relation between the reference voltage and the remaining offset voltage.

The logic control may be implemented by an integrated circuit that performs desired operation based on receiving an input of a detected remaining offset voltage. The logic control may be implemented by a programmable logic integrated circuit or by an application-specific integrated circuit.

According to an alternative, the control unit may comprise a processing unit which is configured to determine reference voltage compensation based on the detected remaining offset voltage. The processing unit may be implemented as a general-purpose processing unit, which may execute software for controlling the processing unit to determine reference voltage compensation based on the detected remaining offset voltage.

However, since an operation to be performed by the control unit for determining reference voltage compensation is fairly simple, it may be advantageous to use a logic control specifically programmed to perform the desired operation.

According to an embodiment, the control unit is configured to activate reference voltage compensation on condition that an absolute value of the remaining offset voltage exceeds a threshold value.

This implies that reference voltage compensation need only be activated when the remaining offset voltage is outside a safe window. Hence, the control unit need only activate the adaptation unit when needed in order to avoid offset voltage on the electrode exceeding a safe window. Thus, control of the offset voltage may be provided an efficient manner.

According to an embodiment, the control unit comprises a multi-level quantizer for comparing the detected remaining offset voltage at least to an upper threshold value and a lower threshold value.

The multi-level quantizer provides a simple manner of detecting whether the remaining offset voltage is within the safe window. The multi-level quantizer may be connected to the logic control such that the logic control may receive input from the multi-level quantizer based on the comparison of the detected remaining offset voltage to threshold values.

The multi-level quantizer may thus provide quantized input indicating a range to which a value of the remaining offset voltage belongs. The quantized input is suitable for the logic control.

The multi-level quantizer may provide comparison of the remaining offset voltage to the upper threshold value and the lower threshold value. The upper threshold value may be a positive value and the lower threshold value may be a negative value. For instance, the upper threshold value and the lower threshold value may have the same magnitude, such that the upper threshold value and the lower threshold value may allow the multi-level quantizer to determine whether the absolute value of the remaining offset voltage is within the safe window.

According to an embodiment, the multi-level quantizer may comprise a first comparator for comparing the detected remaining offset voltage to the upper threshold value and a second comparator for comparing the detected remaining offset voltage to the lower threshold value.

However, it should be realized that the multi-level quantizer may compare the detected remaining offset voltage to further threshold values. This may enable the control unit to provide a more accurate control of the reference voltage taking several different levels of the remaining offset voltage into account.

According to an embodiment, the control unit comprises a switch for controlling the control unit to be active between bursts of the stimulation signal.

The switch may be used such that the control unit is only connected to the output of the stimulator circuit between bursts of the stimulation signal. Thus, the remaining offset voltage is only detected between bursts.

For instance, if the offset voltage detection element is implemented as a resistor voltage divider, a resistor will keep conducting current from the common mode voltage of the stimulation signal to ground. Thus, thanks to using a switch to disconnect the control unit from the output of the stimulator circuit during bursts, the control unit will not impact electrode voltage during bursts.

In addition, power consumption of the stimulator circuit may be limited thanks to the control unit only being active between bursts of the stimulation signal.

According to an embodiment, the control unit is configured to control the compensation unit to be active or inactive during a coming burst based on determining whether the remaining offset voltage is within a range defining a safe window.

The control unit may be used for determining whether the compensation unit need to be at all active during a burst. The compensation unit provides compensation of an unbalanced charge of the stimulation signal during bursts. However, the compensation may not need to be necessarily used during each burst in order to maintain the offset voltage at the electrode within a safety level. Thus, the control unit may be configured to provide a duty control of the compensation unit to control whether the compensation unit is to be active during a coming burst of the stimulation signal.

This allows the compensation unit to be active only when needed, which may ensure that power consumption of the stimulator circuit is limited.

According to an embodiment, the compensation unit comprises a common mode voltage monitoring element configured to monitor a common mode voltage based on the stimulation signal, and a charge balancing element configured to generate a feedback current signal based on the common mode voltage.

The common mode voltage monitoring element may be configured to monitor the common mode voltage at the output of the stimulator circuit.

The charge balancing element may be configured to compare the common mode voltage to the reference voltage and generate the feedback current signal in dependence of a difference between the common mode voltage and the reference voltage. The feedback current signal may be the compensation current signal that is provided to the output of the stimulator circuit. However, the feedback current signal may alternatively be further processed (e.g., amplified) for generating the compensation current signal.

The common mode voltage monitoring may be provided by a low pass filter. However, the common mode voltage may change slowly in relation to a frequency of the stimulation signal, where the change of the common mode voltage may be based on a small unbalance between positive and negative parts of the waveform. Thus, if a low pass filter is to be used, the filtering may need to use a low cut-off frequency which can require a large circuit area.

According to an embodiment, the common mode voltage monitoring element is configured to perform extreme point detection of the stimulation signal for determining an unbalance of the common mode voltage based on the stimulation signal.

This implies that the common mode voltage may be detected using a circuit which may not require a large area. Thus, the stimulator circuit may be compact.

The common mode voltage monitoring element may be configured to detect a maximum and/or a minimum of the stimulation signal. The common mode voltage monitoring element may use the extreme point detection, such that at beginning of compensation a trend of the common mode voltage is monitored, which may be used for generating the compensation current signal.

According to an embodiment, the common mode voltage monitoring element comprises a maximum point detection element for detecting local maxima of the stimulation signal, a minimum point detection element for detecting local minima of the stimulation signal, and an averaging element for determining an average based on detected local maxima and detected local minima for monitoring the common mode voltage.

According to an embodiment, the charge balancing element comprises an amplifier configured to receive the common mode voltage and the reference voltage and configured to generate the feedback current signal based on a difference between the common mode voltage and the reference voltage.

This is a suitable manner of determining feedback for forming the compensation current signal to be provided to the output of the stimulator circuit.

According to an embodiment, the compensation unit comprises an attenuator configured to attenuate the stimulation signal, wherein the common mode voltage monitoring element is configured to monitor the common mode voltage based on an attenuated stimulation signal received from the attenuator.

An output signal swing at an electrode receiving the stimulator signal may be large, at least for particular applications, such as when the stimulator circuit is used for peripheral nerve stimulation.

Thanks to the compensation unit comprising the attenuator, the compensation unit may generate the compensation current signal in a power-efficient manner. Thanks to the stimulation signal being attenuated, the common mode voltage monitoring element is not exposed to large voltage swings, such that power consumption of the common mode voltage monitoring element may be limited.

The compensation unit may further be configured to initially generate a feedback current based on the attenuated stimulation signal such that the generation of the feedback current may be performed in a power efficient manner.

Thus, the charge balancing element may be provided as a transconductance amplifier for generating the feedback current signal based on the difference between the common mode voltage and the reference voltage.

The feedback current signal may be used for generating the compensation current signal to be output by the compensation unit. The transconductance amplifier may thus be configured to convert a determined common mode voltage into a feedback current signal.

The transconductance amplifier may need a high transconductance in order for the compensation unit to provide good compensation. Thus, power consumption of the transconductance amplifier may be relatively large and the transconductance amplifier advantageously determines the feedback current signal based on the attenuated stimulation signal. This implies that the transconductance amplifier may use a low voltage supply in order for power consumption to be limited.

As used herein, the term "low voltage" may refer to a voltage suitable for typical use with integrated circuits. Thus, a low voltage may be a voltage smaller than 5 V, such as smaller than 3.5 V. Correspondingly, a voltage larger than 5 V may be referred to herein as a "high voltage".

According to an embodiment, the compensation unit further comprises a current output stage configured to amplify the feedback current signal for forming the compensation current signal.

Thus, the compensation unit may be configured to generate the compensation current signal via the current output stage. The current output stage may be implemented with a high voltage supply and may provide a high output impedance. This implies that the current output stage may be compatible with large output signal swings of the stimulator circuit.

According to an embodiment, the compensation current signal is a direct current (DC) signal.

When a compensation loop formed by the compensation unit is stable, the compensation current signal will be a DC signal. This implies that the compensation current signal will not affect performance of the AC stimulation signal output by the stimulator circuit and will thus not affect a stimulation of a living being. For instance, if stimulation of a living being is to be performed by interferential stimulation, the DC signal provided by the compensation current signal will have no effect on the interferential stimulation.

According to an embodiment, the stimulation signal generating unit comprises a current source and a current sink for generating the stimulation signal, wherein the current source and the current sink are independent components.

Thanks to using independent components of the current source and the current sink, crosstalk between two stimulator circuits, which may be used for example in interferential stimulation, may be avoided during stimulation.

However, using independent components, there is a higher risk for an unbalanced charge being provided by the waveform of the stimulation signal, since the current source and the current sink may exhibit different nonideal characteristics.

Hence, the stimulator circuit providing a compensation of an unbalanced charge of the stimulation signal may be particularly useful when the current source and the current sink are independent components.

According to a second aspect, there is provided a system for providing stimulation of a brain and/or a nerve of a living being, said system comprising: the stimulator circuit according to the first aspect; and at least one electrode connected to the stimulator circuit for receiving the compensated stimulation signal from the output of the stimulator circuit, wherein the at least one electrode is configured to be arranged in relation to the brain and/or the nerve for transmitting the compensated stimulation signal into the brain and/or the nerve.

Effects and features of this second aspect are largely analogous to those described above in connection with the first aspect. Embodiments mentioned in relation to the first aspect are largely compatible with the second aspect.

Thus, the stimulator circuit may be part of a system for providing stimulation of a brain and/or a nerve of a living being, such as a human being or an animal. The stimulator circuit may thus provide the compensated stimulation signal to an electrode located for transmitting the compensated stimulation signal to the living being. The stimulator circuit may be used in any application where an AC stimulation signal is to be provided to the living being.

The compensated stimulation signal may be transmitted into the brain and/or a nerve based on one electrode connected to the stimulator circuit and a reference electrode. The reference electrode may be a common reference electrode shared by a plurality of stimulator circuits.

The compensated stimulation signal may alternatively be provided by the stimulator circuit to a pair of electrodes for transmitting the compensated stimulation signal into the brain and/or nerve.

It should further be realized that the system may be configured to both transmit the compensated stimulation signal into the brain and/or the nerve and to detect signals propagating in the brain and/or the nerve, such as signals affected or triggered by the compensated stimulation signal.

Thus, the system may comprise additional electrodes for detecting signals in the brain and/or the nerve. However, it should be realized that the same electrodes may be used for transmitting signals into the brain and/or the nerve and for receiving signals. For instance, the transmitted signal is a current signal, whereas the received signal may be a voltage signal allowing the same electrode to be used for both purposes.

According to a third aspect, there is provided a system for providing temporal interference stimulation of a brain and/or a nerve of a living being, said system comprising: a first stimulator circuit according to the first aspect for forming a first compensated stimulation signal at the output of the first stimulator circuit; at least one first electrode connected to the first stimulator circuit for receiving the first compensated stimulation signal from the output of the first stimulator circuit, wherein the at least one first electrode is configured to be arranged in a first relation to the brain and/or the nerve for transmitting the first compensated stimulation signal into the brain and/or the nerve; a second stimulator circuit according to the first aspect for forming a second compensated stimulation signal at the output of the second stimulator circuit; and at least one second electrode connected to the second stimulator circuit for receiving the second compensated stimulation signal from the output of the second stimulator circuit, wherein the at least one second electrode is configured to be arranged in a second relation to the brain and/or the nerve for transmitting the second compensated stimulation signal into the brain and/or the nerve; wherein the at least one first electrode and the at least one second electrode are configured to be arranged in relation to the brain and/or the nerve for forming an interferential stimulation signal in the brain and/or the nerve based on interference between the first compensated stimulation signal and the second compensated stimulation signal.

Effects and features of this third aspect are largely analogous to those described above in connection with the first and second aspects. Embodiments mentioned in relation to the first and second aspects are largely compatible with the third aspect.

Thus, a system for temporal interference stimulation may comprise at least two stimulator circuits for generating at least a first and a second compensated stimulation signal to be used for forming the interferential stimulation signal.

Each stimulator circuit may generate a compensated stimulation signal that comprises a sequence of temporally separated bursts, wherein each burst is a continuous signal being output for a period of time. The interferential stimulation signal may be generated based on interference of the compensated stimulation signals.

The system therefore advantageously makes use of the stimulator circuit according to the first aspect for each of the stimulator circuits of the system, to ensure that build-up of offset voltage at the electrodes is avoided during bursts of the stimulation signals and over the sequence of separated bursts.

Each stimulator circuit may be associated with a respective electrode. As discussed above for the second aspect, the compensated stimulation signal may be output to a single electrode, wherein a reference electrode may further be used, which reference electrode may be common to two or more stimulator circuits. Alternatively, the compensated stimulation signal may be output to a pair of electrodes, wherein each stimulator circuit is associated with a respective pair of electrodes.

As yet another alternative, a first and a second pair of stimulator circuits may be used for output of stimulation signals to a first and a second pair of electrodes. The first stimulator circuit may thus be combined with a third stimulator circuit to form the first pair of stimulator circuits and the second stimulator circuit may be combined with a fourth stimulator circuit to form the second pair of stimulator circuits. The first stimulator circuit and the third stimulator circuit may be configured to receive an identical current waveform, which may be copied and optionally amplified by a current source and a current sink. The first stimulator circuit and the third stimulator circuit device may be controlled such that the first stimulator device may enable the current source when the second stimulator device enables the current sink, and vice versa. Each of the first stimulator circuit and the third stimulator circuit may be connected to a respective electrode of the first pair of electrodes which may thus receive compensated stimulation signals that are in anti-phase for forming a stimulation signal to be transmitted into the brain and/or the nerve.

It should further be realized that the stimulator circuit may be connected to a set of electrodes, such that the electrode to be used for transmitting of the compensated stimulation signal into the brain and/or nerve may be dynamically selected when the system is used.

It should be realized that the system may comprise more than two stimulator circuits for output of more than two compensated stimulation signals. A number of stimulator circuits of the system may be dependent on the stimulation to be provided. For instance, in some embodiments, the system may comprise more than two stimulator circuits for generating more than two compensated stimulation signals for causing an interferential stimulation signal to be formed based on more than two compensated stimulation signals.

According to a fourth aspect, there is provided a method for providing a compensated stimulation signal, said method comprising: generating a stimulation signal and providing the stimulation signal to an output of a stimulator circuit, wherein the stimulation signal comprises a sequence of temporally separated bursts, wherein each burst comprises an alternating current, AC, signal having a sinusoidal-like waveform; during a burst of the stimulation signal, generating a compensation current signal for charge balancing and providing the compensation current signal to the output of the stimulator circuit for compensating an unbalanced charge of the stimulation signal and forming a compensated stimulation signal at the output of the stimulator circuit, wherein the compensation current signal is determined based on a common mode voltage of the stimulation signal and a reference voltage; and controlling the reference voltage in dependence of a remaining offset voltage at the output of the stimulator circuit between bursts of the stimulation signal.

In particular, the method may be performed in the stimulator circuit of the first aspect or in the system according to the second or third aspects.

Effects and features of this fourth aspect are largely analogous to those described above in connection with the first, second, and third aspects. Embodiments mentioned in relation to the first, second, and third aspects are largely compatible with the fourth aspect.

Thanks to the method, a compensated stimulation signal may be provided to avoid build-up of offset voltage at an electrode during bursts of the stimulation signals and over the sequence of separated bursts.

BRIEF DESCRIPTION OF THE DRAWINGS

The above, as well as additional objects, features, and advantages of the present description, will be better understood through the following illustrative and non-limiting detailed description, with reference to the appended drawings. In the drawings like reference numerals will be used for like elements unless stated otherwise.

DETAILED DESCRIPTION

Figure 1:
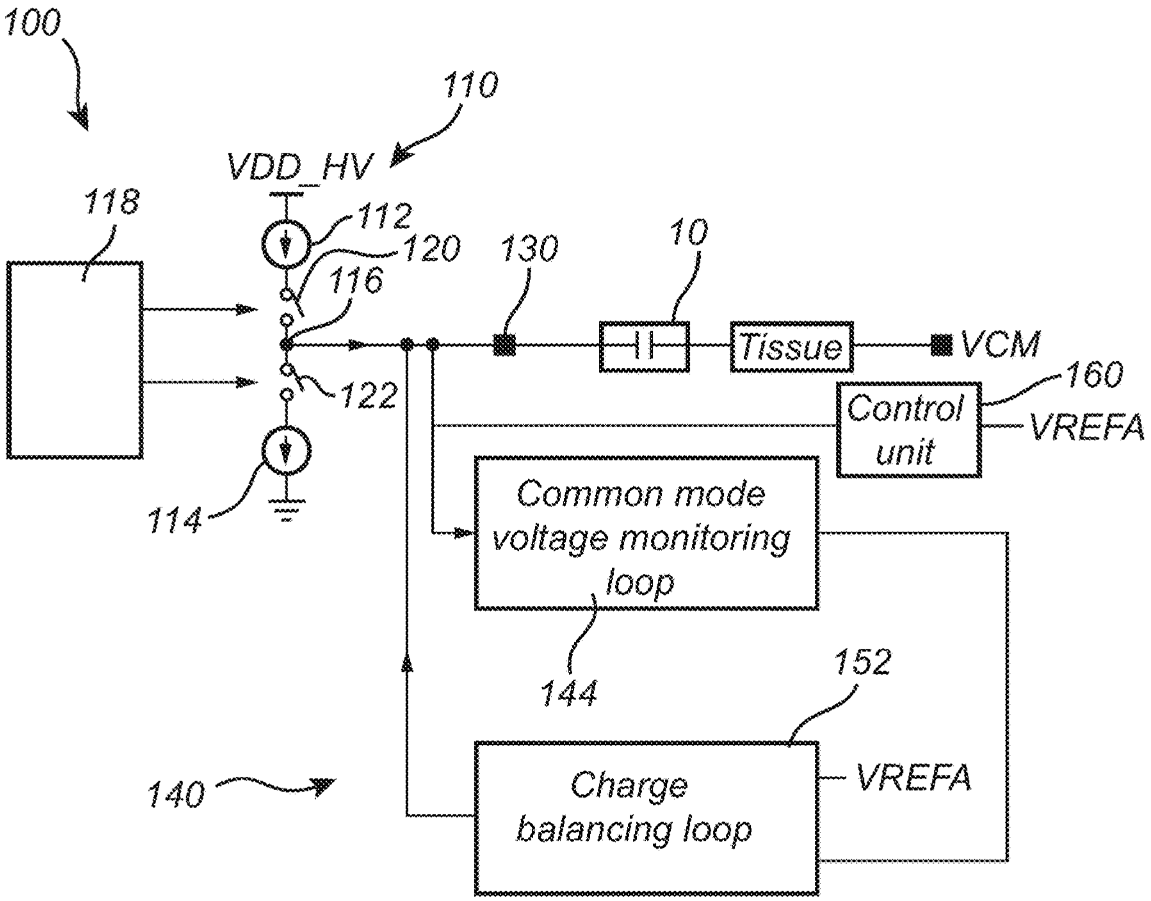
FIG. 1 is a schematic view of a stimulator circuit according to a first embodiment.

Referring now to FIG. 1, a stimulator circuit 100 according to a first embodiment will be described.

The stimulator circuit 100 comprises a stimulation generating unit 110 configured to generate a stimulation signal. The stimulation generating unit 110 may comprise a current source 112 and a current sink 114. The current source 112 may be connected between a supply voltage and an output node 116 and the current sink 114 may be connected between ground and the output node 116.

The stimulation generating unit 110 may further comprise a stimulation controller 118 which may provide digital control of a first switch 120 arranged between the current source 112 and the output node 116 and a second switch 122 arranged between the current sink 114 and the output node 116. The control unit 118 may thus control which of the current source 112 and the current sink 114 is connected to the output node 116.

The current source 112 and the current sink 114 may thus form independent components for generating an AC stimulation signal at the output node 116. The use of independent components may avoid crosstalk between two stimulator circuits, which may be used for example for providing interferential stimulation, during output of a stimulation signal at the output node 116.

The output node 116 may further be connected to an output 130 of the stimulator circuit 100. The output 130 may further be connected, e.g., to an electrode 10 for providing the stimulation signal to a living being. It should be realized that the electrode 10 may not necessarily be part of the stimulator circuit 100.

The stimulation signal generating unit 110 may be configured to output the stimulation signal at the output node 116. The stimulation signal may be an AC signal having a sinusoidal-like waveform, such as a pure sinusoidal waveform, a pseudo-sinusoidal waveform, a modified sinusoidal waveform, or a multi-level waveform approximating a sinusoidal waveform.

For instance, the stimulation signal generating unit 110 may be utilized in temporal interference stimulation. Temporal interference stimulation uses multiple stimulator circuits for providing multiple AC signals having sinusoidal-like waveforms, wherein interference between the multiple AC signals allows spatially selecting a location for stimulation in a brain and/or a nerve of a living being. In particular, a maximum amplitude of the interferential stimulation signal may be provided inside the brain and/or the nerve such that stimulation may be provided deep within the brain and/or a nerve by signals output by electrodes arranged externally to the brain and/or the nerve.

Temporal interference stimulation may be provided by duty-cycled stimulation signals, such that the stimulation signal may comprise a sequence of temporally separated bursts, wherein each burst comprises an AC signal having a sinusoidal-like waveform. For instance, a stimulation signal having bursts with a duration in a range of 10 μs-5 ms may be used.

Figure 2:
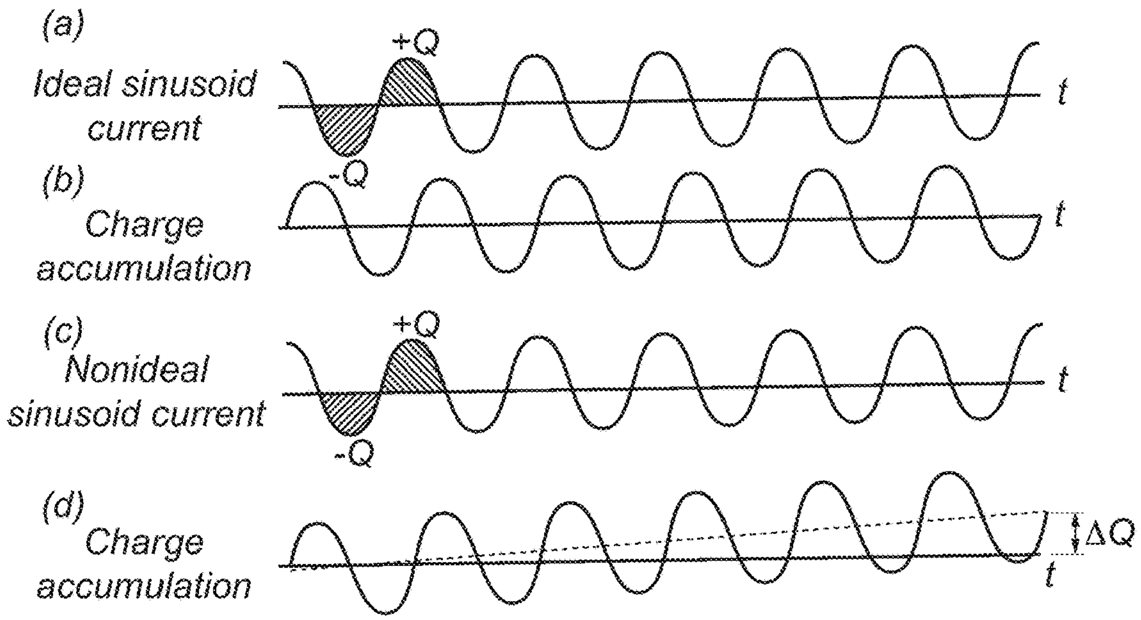
FIG. 2 shows charts illustrating an unbalanced charge provided to an output during a burst of a stimulation signal.

Referring now to FIG. 2, charge accumulation at an electrode 10 connected to the output 130 of the stimulator circuit 100 is illustrated during a single burst of a stimulation signal. FIG. 2 shows in chart (a) an ideal sinusoidal current waveform. As indicated in chart (a), a negative charge −Q provided to the electrode 10 at a negative part of the sinusoidal waveform corresponds to a positive charge +Q provided to the electrode 10 at a positive part of the sinusoidal waveform. Thus, as illustrated in chart (b) of FIG. 2, during a full period of the sinusoidal waveform, no charge accumulation occurs.

FIG. 2 shows in chart (c) a nonideal sinusoidal current waveform. As indicated in chart (c), a negative charge −Q provided to the electrode 10 at a negative part of the sinusoidal waveform is smaller than a positive charge +Q provided to the electrode 10 at a positive part of the sinusoidal waveform. Thus, as illustrated in chart (d) of FIG. 2, a net charge accumulation will occur during a full period of the sinusoidal waveform. This implies that if the stimulation signal is provided continuously for a period of time a large charge accumulation may occur.

Referring again to FIG. 1, the stimulator circuit 100 further comprises a compensation unit 140. The compensation unit 140 may be connected between the stimulation signal generating unit 110 and the output 130 of the stimulator circuit 100. The compensation unit 140 may form a feedback loop for performing charge balancing during output of a burst of the stimulation signal by the stimulation signal generating unit 110 to the output 130.

The compensation unit 140 may thus be configured to provide a compensation current signal to the output 130 for compensating an unbalanced charge of the stimulation signal. It should be realized that the compensation unit 140 may not necessarily perfectly balance charge accumulation at the output 130 but may at least reduce charge accumulation so as to avoid risks involved with large offset voltage build-up at the electrode 10.

The compensation unit 140 may be configured to regulate a common mode voltage of the AC signal at the output 130 of the stimulator circuit 100. As illustrated in FIG. 1, the output 130 may be connected to tissue of a living being via the electrode 10 such that a current signal from the stimulation signal generating unit 110 is converted to a voltage signal. The common mode voltage may thus be based on the stimulation signal.

The compensation unit 140 may comprise a common mode voltage monitoring element 144, which is configured to monitor the common mode voltage at the output 130. The common mode voltage monitoring element 144 may thus be connected to receive a signal of the output 130 of the stimulator circuit 100.

The compensation unit 140 may further comprise a charge balancing element 152 which may be configured to generate the compensation current signal based on the common mode voltage monitored by the common mode voltage monitoring element 144. The compensation unit 140 may be configured to output the compensation current signal to the output 130 of the stimulator circuit 100 for forming a compensated stimulation signal at the output 130. Thus, the stimulation signal in combination with the compensation current signal may form the compensated stimulation signal at the output 130.

The charge balancing element 144 may be configured to generate the compensation current signal based on a difference between the common mode voltage and a reference voltage. Thus, a direct current (DC) signal may be generated to compensate for any unbalanced charge of a burst of the stimulation signal.

Even though compensation of unbalanced charges during a burst is provided, an offset voltage at the output 130 of the stimulator circuit 100 may still remain after a burst. This implies that build-up of an offset voltage at the output 130 of the stimulator circuit 100 may occur over the sequence of temporally separated bursts of the stimulation signal. The stimulator circuit 100 may be configured to compensate for a remaining offset voltage at the output 130 of the stimulator circuit 100 between bursts of the stimulation signal.

The stimulator circuit 100 further comprises a control unit 160, which is used for providing compensation for the remaining offset voltage.

The control unit 160 is configured to control the reference voltage which is used by the compensation unit 140. The control unit 160 is configured to control the reference voltage in dependence of the remaining offset voltage at the output 130 of the stimulator circuit 100 between bursts of the stimulation signal.

The reference voltage may be controlled such that the compensation current signal to be provided during a coming burst of the stimulation signal may be adjusted so as to compensate for the remaining offset voltage. Thanks to controlling the reference voltage, the remaining offset voltage may be compensated for without a need of providing a reset for removing the remaining offset voltage. This implies that the remaining offset voltage may be removed without causing any reset artefacts (spikes) and without causing a recovery time for removing the remaining offset voltage. Hence, since the stimulator circuit 100 does not provide a separate reset process for resetting the output 130 of the stimulator circuit 100, there is no unnecessary delay between bursts of the stimulation signal. Also, it is possible to record any possible response from the brain and/or the nerve immediately after the burst, without such recording being affected by a reset artefact.

If the remaining offset voltage is positive, the reference voltage may be decreased so as to force the compensation unit 140 to generate a negative compensation current signal of a larger amplitude, whereby the remaining offset voltage may be removed from the output 130. If the remaining offset voltage is negative, the reference voltage may be increased so as to force the compensation unit 140 to generate a positive compensation current signal of a larger amplitude, whereby the remaining offset voltage may be removed from the output 130.

Figure 3:
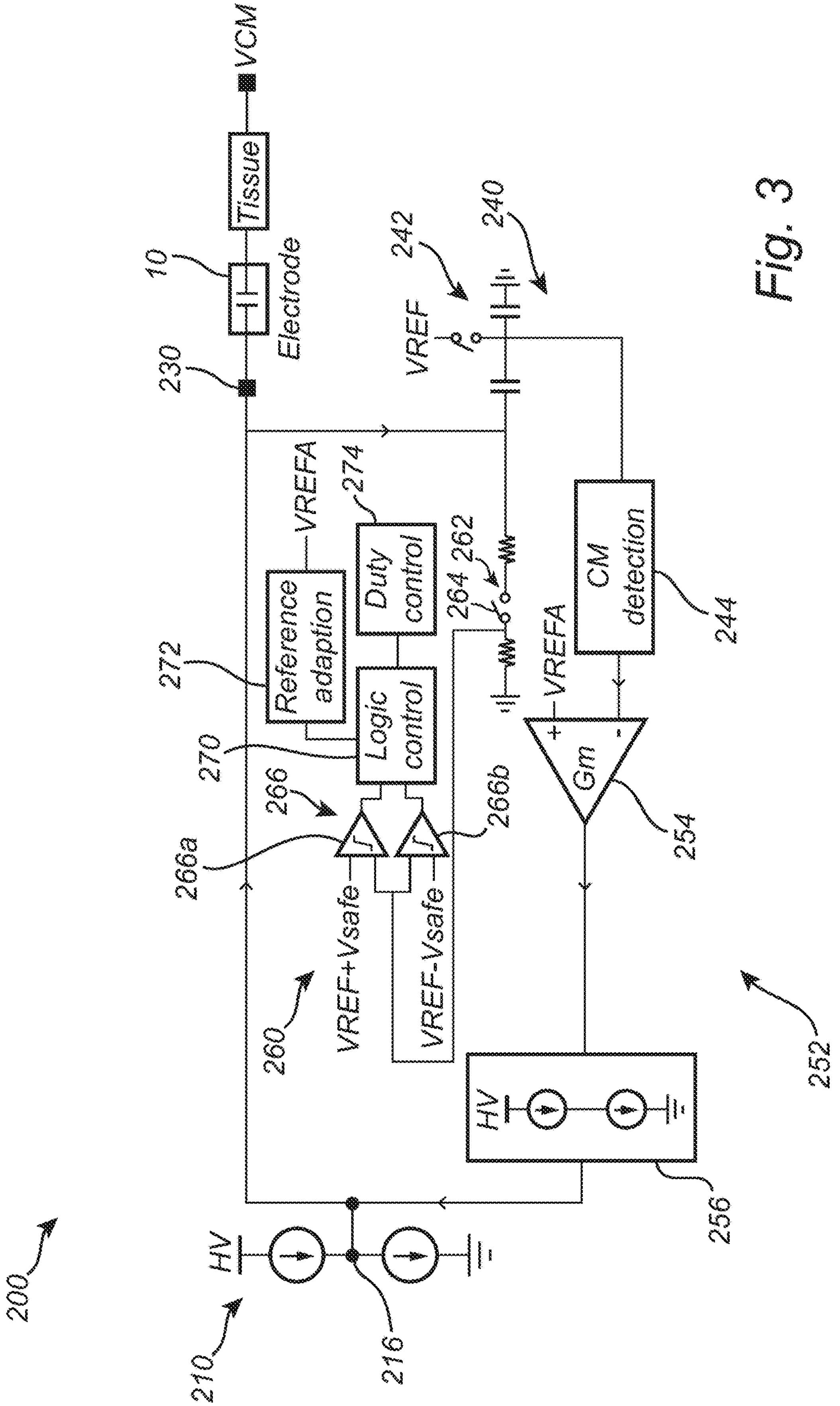
FIG. 3 is a schematic view of a stimulator circuit according to a second embodiment.

Referring now to FIG. 3, a stimulator circuit 200 according to a second embodiment will be described. The stimulator circuit 200 is illustrated with more details compared to the stimulator circuit 100. It should be realized that these details may be utilized in the stimulator circuit 200 as well.

The stimulator circuit 200 comprises a stimulation signal generating unit 210 similar to the stimulation signal generating unit 110 described above. The stimulation signal generating unit 210 may be configured to output the stimulation signal at an output node 216.

The output node 216 may further be connected to an output 230 of the stimulator circuit 200. The output 230 may further be connected, e.g., to an electrode 10 for providing the stimulation signal to a living being.

The stimulator circuit 200 comprises a compensation unit 240 for generating a compensation current signal for charge balancing during a burst of the stimulation signal. The stimulator circuit 200 further comprises a control unit 260 for controlling a reference voltage so as to control the compensation provided by the compensation current signal for compensating for a remaining offset voltage between bursts of the stimulation signal.

The control unit 260 comprises an offset voltage detection element 262 which detects the remaining offset voltage. As shown in FIG. 3, the offset voltage detection element 262 may be implemented as a simple passive component, providing detection of the remaining offset voltage in a power-efficient manner. However, it should be realized that an active component may alternatively be used.

The offset voltage detection element 262 in the second embodiment is a resistor voltage divider comprising two resistors in series between the output 230 and ground. The offset voltage detection element 262 provides an output at a node between the two resistors, representing a detected remaining offset voltage.

The control unit 260 may comprise a switch 264 arranged between the output 230 and the node at which output from the offset voltage detection element 262 is provided. The switch 264 may thus selectively disconnect the resistor voltage divider from the output 230 or connect the resistor voltage divider to the output 230. This may be used for controlling whether the control unit 260 is active or not. The switch 264 may be closed between bursts of the stimulation signal such that the control unit 260 is active between bursts of the stimulation signal, whereas the switch 264 may be opened during bursts of the stimulation signal such that the control unit 260 is not active during bursts.

The control unit 260 may further comprise a multi-level quantizer 266 for comparing the detected remaining offset voltage to at least two threshold values. The multi-level quantizer 266 may thus be able to determine a range among a plurality of ranges to which the detected remaining offset voltage belongs.

As shown in FIG. 3, the multi-level quantizer 266 may comprise a first comparator 266*a* for comparing the detected remaining offset voltage to an upper threshold value and a second comparator 266*b* for comparing the detected remaining offset voltage to a lower threshold value. Based on the first and the second comparator 266*a*, 266*b*, the multi-level quantizer 266 may thus determine whether the detected remaining offset voltage is smaller than the lower threshold value, is between the lower threshold value and the upper threshold value or is higher than the upper threshold value.

It should be realized that the multi-level quantizer 266 may compare the detected remaining offset voltage to more threshold values for more accurately representing a range to which the detected remaining offset voltage belongs.

The control unit 260 may further comprise a logic control 270. The logic control 270 may receive input from the multi-level quantizer 266. Thus, the logic control 270 may receive a quantized input allowing the logic control 270 to provide control of the reference voltage in dependence of the detected remaining offset voltage using a relatively low complexity of the logic control 270.

The logic control 270 may for instance be implemented as a programmable integrated circuit or as an application-specific integrated circuit.

The logic control 270 may be configured such that the logic control 270 may determine a reference voltage compensation to be provide based on the detected remaining offset voltage. The logic control 270 may thus output instructions that cause a desired reference voltage compensation to be performed.

The control unit 260 may further comprise an adaptation unit 272. The adaptation unit 272 may be connected to the logic control 270 such that the logic control 270 may provide instructions to control the adaptation unit 272 to execute the determined reference voltage compensation.

The adaptation unit 272 may be configured to provide adjustment of the reference voltage using a fixed adjustment step. Thus, the adaptation unit 272 may receive instructions increase the reference voltage or decrease the reference voltage by the adjustment step. The adaptation unit 272 may be configured to apply the adjustment and, thereafter, output the reference voltage having an adjusted value.

The adaptation unit 272 may be activated only when an adjustment of the reference voltage is needed. Thus, the logic control 270 may send instructions to the adaptation unit 272 only when an adjustment is to be performed. The logic control 270 may for instance be configured to send two different types of enable signals to the adaptation unit 272 based on the need for increasing the reference voltage or for decreasing the reference voltage.

It should be realized that the logic control 270 and the adaptation unit 272 may be configured in different manners for providing a different relation between the reference voltage output by the adaptation unit 272 and the detected remaining offset voltage. For instance, a more linear relation between the reference voltage and the detected remaining offset voltage may be provided.

The control unit 260 may further be configured to determine whether the compensation unit 240 needs to be active during a coming burst of the stimulation signal. For instance, if there is a small mismatch between negative parts and positive parts of the sinusoidal waveform of a burst, the compensation unit 240 need not be active during each burst while build-up of offset voltage at the output 230 may still be within a safe range, i.e. without causing any safety issues to the electrode and/or the tissue.

The control unit 260 may comprise a duty control unit 274, which may receive input from the logic control 270. For instance, the logic control 270 may provide instruction to the duty control unit 274 such as sending an enable signal to the duty control unit 274 when the detected remaining offset voltage is outside a safe window, wherein the safe window may provide some margin to a safe range of the offset voltage at the output 230 of the stimulator circuit 200.

The duty control unit 274 may be configured to output a signal when the compensation unit 240 is to be active during a coming burst. Thus, absence of such a signal from the duty control unit 274 may imply that the compensation unit 240 will be inactive during the coming burst. The duty control unit 274 may be controlled such that the compensation unit 240 may be active or inactive during a coming burst in dependence on whether the remaining offset voltage is or is not within a range defining the safe window.

The stimulator circuit 200 is particularly adapted for use in applications where a large signal swing at the output 230 of the stimulator circuit 200 is desired. For instance, in peripheral nerve stimulation, the signal swing at the output 230 may preferably be in a range of tens of volts. The stimulation signal generating unit 210 may thus be implemented with a high voltage supply, such as 20 V supply voltage, to provide compliance of the stimulation signal generating unit 210 with large signal swings at the output 230.

The stimulation current provided by the stimulation signal generating unit 210 may be up to a few mA. This may imply that the compensation unit 240 may have a large power consumption.

In order for power consumption of the compensation unit 240 to be limited, the compensation unit may thus comprise an attenuator 242 configured to attenuate the signal at the output 230 of the stimulator circuit 200 such that components of the compensation unit 240 may receive an attenuated stimulation signal.

Thus, the common mode monitoring element 244 may be configured to operate at low voltage supply to monitor the common mode voltage based on an attenuated stimulation signal received from the attenuator 242.

In addition, the charge balancing element 252 may comprise a transconductance amplifier 254 that is configured to operate at low voltage supply and a current output stage 256 compatible with a high voltage signal swing.

The transconductance amplifier 254 may be configured to generate a feedback current signal based on a difference between the common mode voltage of the attenuated stimulation signal and the reference voltage. Thus, the feedback current signal may be a DC providing an indication of compensation needed for compensating any unbalanced charge of a burst of the stimulation signal. The charge balancing element 252 may further comprise a current output stage 256, which may amplify the feedback current signal and generate the compensation current signal to be provided at the output 230 of the stimulator circuit 230.

Thus, it is realized that high voltage supply is not necessary for determining a feedback current for compensating an unbalanced charge. The attenuator 242 may be configured to attenuate the high voltage signal at the output 230 of the stimulator circuit 200.

The attenuator 242 may be configured to attenuate a received signal by a factor F to allow a lower supply voltage to be used in components processing the attenuated signal.

The attenuator 242 may be a passive component (such as a resistor/capacitor divider) or an active component. According to a preferred embodiment shown in FIG. 3, the attenuator 242 is a capacitor divider. A capacitor divider is preferred over a resistor divider since a resistor conducts current from the common mode voltage to ground.

The capacitor divider comprises two capacitors connected in series between the output 230 of the stimulator circuit 200 and ground. The capacitor divider further provides an output at a node between the two capacitors, such that an attenuated stimulation signal is provided at the node.

The capacitor divider may be connected via a reset switch to a second reference voltage, $V_{REF}$. Thus, during periods between bursts of the stimulation signal, the capacitor divider may be reset to the second reference voltage $V_{REF}$ to minimize impact of leakage current on the capacitors and increase reliability of attenuation of the AC stimulation signal. This may allow using small size capacitors, wherein the rest of the node between the capacitors ensures that leakage and drift over time after a few bursts of the stimulation signal is avoided or at least reduced.

The reference voltage used by the capacitor divider is referred to as the second reference voltage in order to distinguish from the reference voltage, which may hereinafter be interchangeably referred to as a first reference voltage and which is used by the charge balancing element 252 for determining the compensation current signal.

The common mode voltage monitoring element 244 may for example comprise a low pass filter for providing monitoring of the common mode voltage.

However, the offset voltage at the output 230 may change very slowly compared to frequency of the sinusoidal waveform. Thus, filtering of the sinusoidal signal may be performed by a high-order or low cut-off frequency filter. Thus, use of a low pass filter may be area consuming. Also, a design of the low pass filter may be complex if a signal swing of the input sinusoidal signal received by the common mode voltage monitoring element 244 goes rail-to-rail.

The common mode voltage monitoring element 244 may be configured to perform extreme point detection of the input signal for determining an unbalance of the common mode voltage. The common mode voltage monitoring element 244 may comprise a maximum point detection element and a minimum point detection element for detecting local maxima and local minima of the input signal. The common mode voltage monitoring element 244 may further comprise an averaging element for determining an average of the input signal based on the detected local maxima and detected local minima. The averaging element may thus output a representation of the common mode voltage.

The charge balancing element 252 may be configured to receive a representation of the common mode voltage from the common mode monitoring element 244. The charge balancing element 252 may comprise a transconductance amplifier 254 which may also operate at low voltage supply for generating a feedback current based on which the compensation current signal may be generated.

The transconductance amplifier 254 may compare the received common mode voltage from the common mode voltage monitoring element 244 to the first reference voltage, $V_{REFA}$. The transconductance amplifier 254 may be configured to generate the feedback current based on a voltage difference between the common mode voltage and the first reference voltage $V_{REFA}$.

The transconductance amplifier 254 may need a high transconductance Gm to provide good compensation based on the voltage difference. Thanks to the transconductance amplifier 254 being operated at low voltage supply, power consumption of the transconductance amplifier 254 may still be limited.

The feedback current from the transconductance amplifier 254 may further be provided to the current output stage 256 of the charge balancing element 252. The current output stage 256 may be configured to mirror or further amplify the feedback current. The current output stage 256 may thus further boost the transconductance Gm using an amplification A, such that the voltage difference detected by the transconductance amplifier 252 may be amplified by A*Gm.

The current output stage 256 may be implemented with a high voltage supply and provide a high output impedance. This implies that the compensation current signal output by the current output stage 256 to the output 230 of the stimulator circuit 200 may be compatible with a large signal swing at the output 230.

The current output stage 256 may be combined with the stimulation signal generating unit 210 using current mirrors. This may provide a compact arrangement of the stimulator circuit 200.

An offset voltage at the output 230 of the stimulator circuit 200 may after compensation be proportional to $I_{mismatch}$*FI(A*Gm), where $I_{mismatch}$ is a current corresponding to mismatch in charges provided to the electrode 10 at the positive and negative parts of the stimulation signal from the stimulation signal generating unit 210. Thus, if the term A*Gm is increased, the offset voltage at the output 230 is decreased.

The compensation unit 240 may be configured to output the compensation current signal as a DC signal. If compensation loop formed by the compensation unit 240 is stable, the compensation current signal will be a DC current. This implies that the compensation current signal may not affect the stimulation provided to the living being. In particular, if the stimulation is to be provided as an interferential stimulation based on interference between two or more stimulation signals, the interference is dependent on frequency of the stimulation signals and a DC signal will not affect the interferential signal. Also, the compensation current is usually a small DC current, such as 1% of 10 mA or 10% of 1 mA, depending on the mismatch. This also implies that the compensation current signal will not affect the stimulation.

As mentioned above, the control unit 260 is configured to control the first reference voltage $V_{REFA}$ so as to compensate for a remaining offset voltage at the output 230 of the stimulator circuit 200. If the first reference voltage $V_{REFA}$ is equal to the second reference voltage $V_{REF}$, the compensation unit 240 will regulate the common mode of the coming burst of the stimulation signal. However, if the first reference voltage $V_{REFA}$ is not equal to the second reference voltage $V_{REF}$, the compensation unit 240 will regulate the common mode of the signal on the electrode 10 to a higher or lower potential with a difference Δ of $\Delta=|(V_{REFA}-V_{REF})\times F|$, where F is the attenuation factor of the capacitor divider, which may be used for removing the remaining offset voltage at the output 230.

According to an exemplifying embodiment, the logic control 270 may be configured to control the offset voltage at the output 230 such that reference voltage compensation is provided when an absolute value of the remaining offset voltage exceeds a threshold value. Thus, a safe window may be defined which provides a margin to a safe range of the offset voltage, i.e. a range within which no safety issues to the electrode 10 and/or the tissue are caused.

The logic control may thus be configured to apply reference voltage compensation as described by the following equations:

$$V_{OS}[n] = V_{OS}[n-1] + V_{error} + V_{comp}[n]$$

$$V_{comp}[n] = \Delta, \text{ if } V_{OS}[n-1] < -V_{safe}$$

-continued $$V_{comp}[n] = -\Delta, \text{ if } V_{OS}[n-1] > V_{safe}$$

$$V_{comp}[n] = 0, \text{ if } -V_{safe} < V_{OS}[n-1] < V_{safe}$$

$$V_{OS}[1] = 0$$

In the above equations, n is an integer number defining how many iterations of a burst of the stimulation signal that have been applied, $V_{OS}[n]$ is the remaining offset voltage after n iterations, $V_{error}$ is the offset voltage introduced by each burst of the stimulation signal, e.g., due to mismatch current or other nonidealities, $V_{comp}[n]$ is the compensation voltage that can be provided to the output 230 at iteration number n of the bursts by changing the reference voltage, and $V_{safe}$ is a defined safe window for the offset voltage.

The duty control unit 274 may be configured such that the compensation unit 240 is not activated when $V_{comp}[n]=0$.

Figure 4:
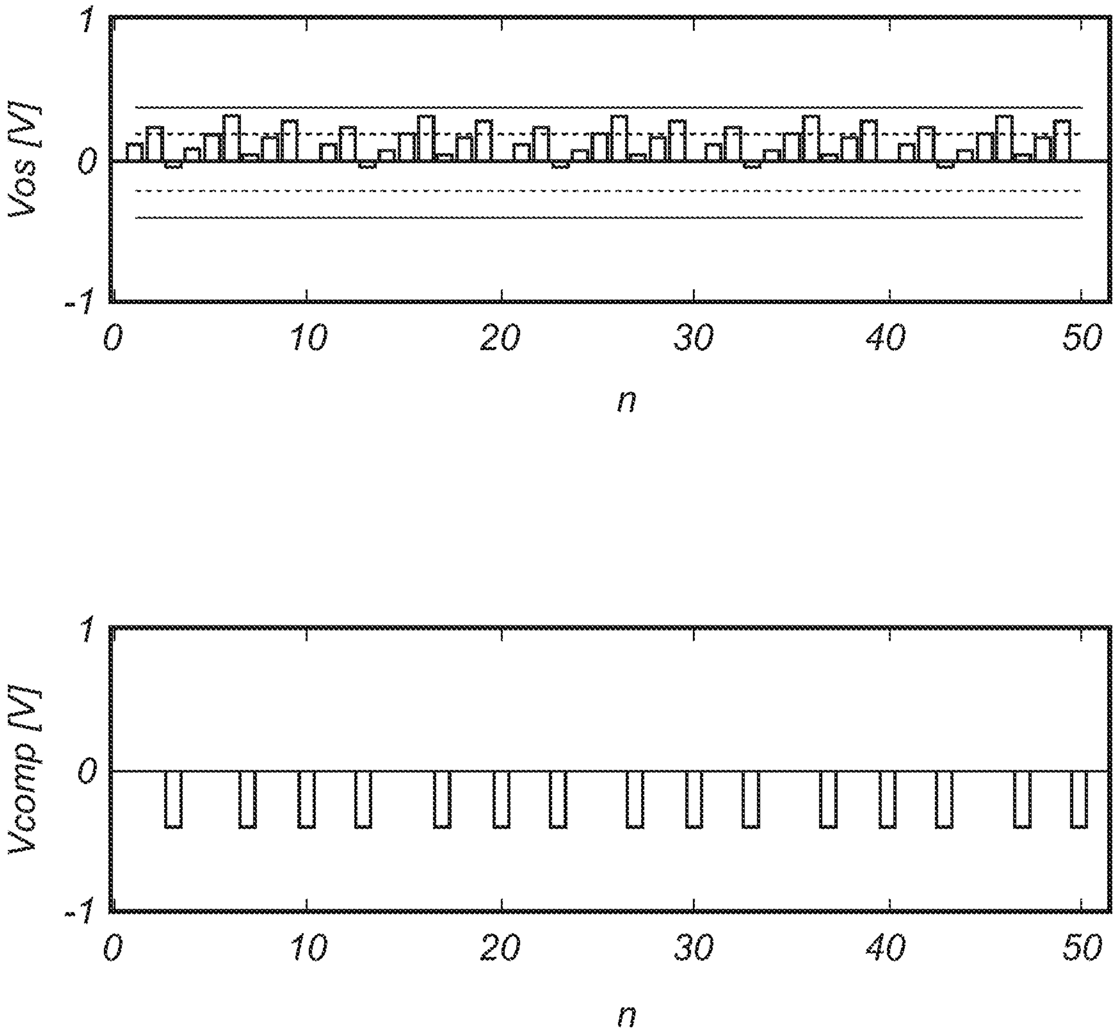
FIG. 4 shows charts illustrating a remaining offset voltage at an output of a stimulator circuit between bursts of a stimulation signal and a reference voltage compensation for compensating for the remaining offset voltage.

Referring now to FIG. 4, an example of how control of the reference voltage may ensure that the compensation unit 240 compensates for a remaining offset voltage is illustrated.

In the upper graph of FIG. 4, the remaining offset voltage $V_{OS}$ [n] is illustrated as a function of a number of iterations n of bursts of the stimulation signal. In the lower graph of FIG. 4, the reference voltage compensation $V_{comp}[n]$ is illustrated as a function of a number of iterations n of bursts of the stimulation signal.

In the upper graph of FIG. 4, solid lines indicate a safe range of absolute values of the offset voltage, i.e. a range within which no safety issues to the electrode 10 and/or the tissue are caused, and dashed lines indicate a safe window corresponding to absolute values of the remaining offset voltage that provide a margin to the safe range of the offset voltage.

In FIG. 4, the compensation provided by the stimulator circuit 200 is simulated for a case in which the accumulated error during each burst is $V_{error}$=120 mV and in which the reference voltage compensation is set to Δ=400 mV. As illustrated in FIG. 4, reference voltage compensation is intermittently needed during the bursts of the stimulation signal. Thus, while the remaining offset voltage is within the safe window, no reference voltage compensation is needed. However, when the remaining offset voltage is outside the safe window, reference voltage compensation is used for the coming burst, whereby the compensation unit 240 is able to compensate for the accumulated remaining offset voltage during the following burst of the stimulation signal.

Figure 5:
FIG. 5 is a schematic view of a system according to an embodiment.

Referring now to FIG. 5, a system 300 for providing stimulation to a living being will be described. The system 300 is shown to provide stimulation of a brain. However, it should be realized that the system 300 may alternatively provide stimulation of a nerve, such as a peripheral nerve.

The system 300 comprises the stimulator circuit 200. It should be realized that the system 300 may comprise any variant of stimulator circuit described above. The system 300 further comprises at least one electrode 302 connected to the output 230 of the stimulator circuit 200.

The at least one electrode 302 may be arranged in or on a carrier 304 adapted to be arranged in relation to the living being, such as being arranged in relation to the brain so as to define a desired relation between the at least one electrode 302 and the brain. The stimulator circuit 200 may also be arranged in the carrier 304, which may facilitate arranging the system 300 on a living being when stimulation is to be provided. However, it should be realized that the stimulator circuit 200 may alternatively be provided in a separate housing from the at least one electrode 302 and the at least one electrode 302 may be connected to the stimulator circuit 200 using wires.

The at least one electrode 302 may be configured to transmit the compensated stimulation signal from the stimulator circuit 200 into the brain of the living being. It should be realized that the stimulation signal may be provided into the brain of the living being based on use of a pair of electrodes. However, the system 300 may comprise only one electrode configured to receive the compensated stimulation signal, whereas another electrode in the pair of electrodes may be a reference electrode, which may be separate from the system 300 and which may be shared by a plurality of stimulator circuits 200.

Figure 6:
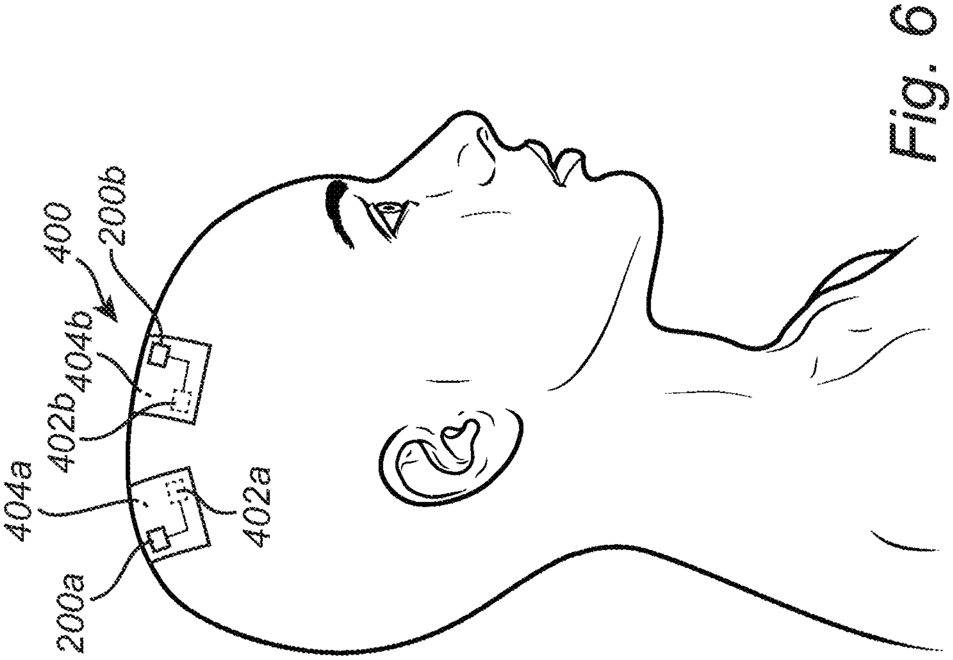
FIG. 6 is a schematic view of a system according to another embodiment.

Referring now to FIG. 6, a system 400 for providing stimulation to a living being will be described. The system 400 is shown to provide stimulation of a brain. However, it should be realized that the system 400 may alternatively provide stimulation of a nerve, such as a peripheral nerve.

The system 400 comprises a first stimulator circuit **200*a* and a second stimulator circuit 200*b*. Each of the first stimulator circuit 200*a* and the second stimulator circuit 200*b* may be any variant of stimulator circuit described above. The system 400 further comprises at least one first electrode 402*a* connected to the output of the first stimulator circuit 200*a* and at least one second electrode 402*b* connected to the output of the second stimulator circuit 200*b***.

The at least one first electrode **402*a* and the at least one second electrode 402*b* may be arranged in or on a common carrier adapted to be arranged in relation to the living being, such as being arranged in relation to the brain so as to define a desired relation between the respective electrode 402*a*, 402*b* and the brain. The first and second stimulator circuits 200*a*, 200*b* may also be arranged in the common carrier. However, according to an alternative, as shown in FIG. 6, the at least one first electrode 402*a* may be arranged in or on a first carrier 404*a* and the first stimulator circuit 200*a* may also be arranged in the first carrier 404*a*. Further, the at least one second electrode 402*b* may be arranged in or on a second carrier 404*b* and the second stimulator circuit 200*b* may also be arranged in the second carrier 404*b***. This may allow larger flexibility in arranging the electrodes in relation to the brain.

Further, it should be realized that the first and second stimulator circuits **200*a*, 200*b* may alternatively be provided in separate housing(s) from the at least one first electrode 402*a* and the at least one second electrode 402*b*. The at least one first electrode 402*a* and the at least one second electrode 402*b* may be connected to the first stimulator circuit 200*a* and the second stimulator circuit 200*b***, respectively, using wires.

The at least one first electrode **402*a* may be configured to transmit a first compensated stimulation signal from the first stimulator circuit 200*a* into the brain of the living being. It should be realized that the stimulation signal may be provided into the brain of the living being based on use of a pair of electrodes. However, the system 400 may comprise only one first electrode 402*a* configured to receive the compensated stimulation signal, whereas another electrode in the pair of electrodes may be a reference electrode, which may be separate from the system 400. Similarly, the at least one second electrode 402*b* may be configured to transmit a second compensated stimulation signal from the second stimulator circuit 200*b* into the brain of the living being. It should be realized that the stimulation signal may be provided into the brain of the living being based on use of a pair of electrodes. However, the system 400 may comprise only one second electrode 402***b* configured to receive the compensated stimulation signal, whereas another electrode in the pair of electrodes may be a reference electrode, which may be separate from the system 400. The reference electrode may be shared for output of the first and second compensated stimulation signals from both the first stimulator circuit 200*a* and the second stimulator circuit 200*b* to the first electrode 402*a* and the second electrode 402*b* in relation to the shared reference electrode.

The at least one first electrode 402*a* and the at least one second electrode 402*b* may be configured to be arranged in relation to the brain such that the first compensated stimulation signal and the second compensated stimulation signal transmitted into the brain may form an interferential stimulation signal in the brain based on interference between the first and the second compensated stimulation signal. The system 400 may thus be configured to provide stimulation of the brain by the interferential stimulation signal.

The system 400 may further comprise a stimulation controller configured to control the first and second stimulator circuits 200*a*, 200*b* such that the first compensated stimulation signal and the second compensated stimulation signal have a desired relation, e.g., being synchronized, in order to form a desired interferential stimulation signal in the brain.

Figure 7:
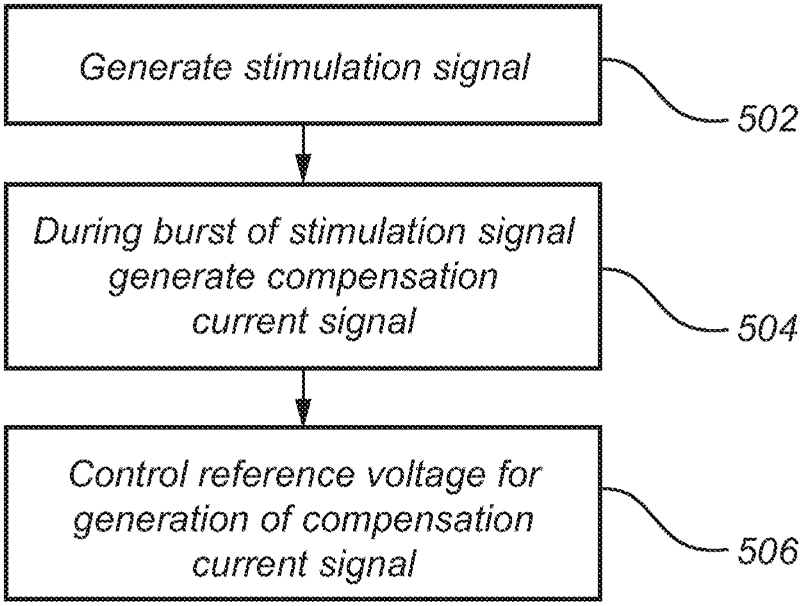
FIG. 7 is a flow chart of a method.

Referring now to FIG. 7, a method for providing a compensated stimulation signal will be described.

The method comprises generating 502 a stimulation signal and providing the stimulation signal to an output. The stimulation signal is a sequence of temporally separated bursts, wherein each burst is an AC signal having a sinusoidal-like waveform. The output may be connected to an electrode configured to transmit a received signal for stimulation of a brain and/or a nerve of a living being.

The method further comprises, during a burst of the stimulation signal, generating 504 a compensation current signal for charge balancing and providing the compensation current signal to the output of the stimulator circuit for compensating an unbalanced charge of the stimulation signal and forming a compensated stimulation signal at the output of the stimulator circuit.

The generating of the compensation current signal may comprise monitoring a common mode voltage based on the stimulation signal, generating a compensation current signal based on the common mode voltage and a reference voltage, and providing the compensation current signal to the output.

The monitoring of the common mode voltage may allow identifying of an unbalanced charge being provided to the output based on the stimulation signal. Thus, the compensation current signal may be generated in dependence of the monitoring of the common mode voltage for compensating an unbalanced charge of the stimulation signal. The compensation current signal being provided to the output implies that the compensated stimulation signal is formed at the output.

The method further comprises controlling 506 the reference voltage in dependence of a remaining offset voltage at the output of the stimulator circuit between bursts of the stimulation signal. The controlling of the reference voltage implies that the generating of the compensation current signal is regulated for a coming burst of the stimulation signal so as to compensate for an unbalanced charge of the stimulation signal during the burst and also compensate for accumulated offset voltage from previous bursts.

In the above the inventive concept has mainly been described with reference to a limited number of examples. However, as is readily appreciated by a person skilled in the art, other examples than the ones disclosed above are equally possible within the scope of the inventive concept, as defined by the appended claims.

The invention claimed is:

1. A stimulator circuit for generating a stimulation signal, said stimulator circuit comprising:

a stimulation signal generating unit configured to generate a stimulation signal and provide the stimulation signal to an output of the stimulator circuit, wherein the stimulation signal comprises a sequence of temporally separated bursts, wherein each burst comprises an alternating current, AC, signal having a sinusoidal-like waveform;

a compensation unit configured to, during a burst of the stimulation signal, generate a compensation current signal for charge balancing and provide the compensation current signal to the output of the stimulator circuit for compensating an unbalanced charge of the stimulation signal and forming a compensated stimulation signal at the output of the stimulator circuit, wherein the compensation unit is configured to determine the compensation current signal based on a common mode voltage of the stimulation signal and a reference voltage; and a control unit configured to control the reference voltage in dependence of a remaining offset voltage at the output of the stimulator circuit between bursts of the stimulation signal.

2. The stimulator circuit according to claim 1, wherein the control unit comprises an offset voltage detection element, wherein the offset voltage detection element is connected to the output of the stimulator circuit for detecting the remaining offset voltage.

3. The stimulator circuit according to claim 2, wherein the control unit further comprises an adaptation unit, which is configured to output the reference voltage to the compensation unit based on the detected remaining offset voltage.

4. The stimulator circuit according to claim 3, wherein the control unit further comprises a logic control programmed to determine reference voltage compensation based on the detected remaining offset voltage, wherein the logic control is configured to control the adaptation unit based on the determined reference voltage compensation.

5. The stimulator circuit according to claim 3, wherein the control unit is configured to activate reference voltage compensation on condition that an absolute value of the remaining offset voltage exceeds a threshold value.

6. The stimulator circuit according to claim 5, wherein the control unit comprises a multi-level quantizer for comparing the detected remaining offset voltage at least to an upper threshold value and a lower threshold value.

7. The stimulator circuit according to claim 1, wherein the control unit comprises a switch for controlling the control unit to be active between bursts of the stimulation signal.

8. The stimulator circuit according to claim 1, wherein the control unit is configured to control the compensation unit to be active or inactive during a coming burst based on determining whether the remaining offset voltage is within a range defining a safe window.

9. The stimulator circuit according to claim 1, wherein the compensation unit comprises a common mode voltage monitoring element configured to monitor a common mode voltage based on the stimulation signal, and a charge balancing element configured to generate a feedback current signal based on the common mode voltage.

10. The stimulator circuit according to claim 9, wherein the charge balancing element comprises an amplifier configured to receive the common mode voltage and the reference voltage and configured to generate the feedback current signal based on a difference between the common mode voltage and the reference voltage.

11. The stimulator circuit according to claim 9, wherein the compensation unit comprises an attenuator configured to attenuate the stimulation signal, wherein the common mode voltage monitoring element is configured to monitor the common mode voltage based on an attenuated stimulation signal received from the attenuator.

12. The stimulator circuit according to claim 1, wherein the stimulation signal generating unit comprises a current source and a current sink for generating the stimulation signal, wherein the current source and the current sink are independent components.

13. A system for providing stimulation of a brain and/or a nerve of a living being, said system comprising:

the stimulator circuit according to claim 1; and at least one electrode connected to the stimulator circuit for receiving the compensated stimulation signal from the output of the stimulator circuit, wherein the at least one electrode is configured to be arranged in relation to the brain and/or the nerve for transmitting the compensated stimulation signal into the brain and/or the nerve.

14. A system for providing temporal interference stimulation of a brain and/or a nerve of a living being, said system comprising:

a first stimulator circuit for generating a stimulation signal, said first stimulator circuit comprising:

a stimulation signal generating unit configured to generate a stimulation signal and provide the stimulation signal to an output of the first stimulator circuit, wherein the stimulation signal comprises a sequence of temporally separated bursts, wherein each burst comprises an alternating current, AC, signal having a sinusoidal-like waveform;

a compensation unit configured to, during a burst of the stimulation signal, generate a compensation current signal for charge balancing and provide the compensation current signal to the output of the first stimulator circuit for compensating an unbalanced charge of the stimulation signal and forming a compensated stimulation signal at the output of the first stimulator circuit, wherein the compensation unit is configured to determine the compensation current signal based on a common mode voltage of the stimulation signal and a reference voltage; and a control unit configured to control the reference voltage in dependence of a remaining offset voltage at the output of the stimulator circuit between bursts of the stimulation signal, wherein the first stimulator circuit is configured for forming a first compensated stimulation signal at the output of the first stimulator circuit;

at least one first electrode connected to the first stimulator circuit for receiving the first compensated stimulation signal from the output of the first stimulator circuit, wherein the at least one first electrode is configured to be arranged in a first relation to the brain and/or the nerve for transmitting the first compensated stimulation signal into the brain and/or the nerve;

a second stimulator circuit according to claim 1 for forming a second compensated stimulation signal at the output of the second stimulator circuit; and at least one second electrode connected to the second stimulator circuit for receiving the second compensated stimulation signal from the output of the second stimulator circuit, wherein the at least one second electrode is configured to be arranged in a second relation to the brain and/or the nerve for transmitting the second compensated stimulation signal into the brain and/or the nerve;

wherein the at least one first electrode and the at least one second electrode are configured to be arranged in relation to the brain and/or the nerve for forming an interferential stimulation signal in the brain and/or the nerve based on interference between the first compensated stimulation signal and the second compensated stimulation signal.

15. A method for providing a compensated stimulation signal, said method comprising:

generating a stimulation signal and providing the stimulation signal to an output of a stimulator circuit, wherein the stimulation signal comprises a sequence of temporally separated bursts, wherein each burst comprises an alternating current, AC, signal having a sinusoidal-like waveform;

during a burst of the stimulation signal, generating a compensation current signal for charge balancing and providing the compensation current signal to the output of the stimulator circuit for compensating an unbalanced charge of the stimulation signal and forming a compensated stimulation signal at the output of the stimulator circuit, wherein the compensation current signal is determined based on a common mode voltage of the stimulation signal and a reference voltage; and controlling the reference voltage in dependence of a remaining offset voltage at the output of the stimulator circuit between bursts of the stimulation signal.

* * * * *